US011737698B2

(12) United States Patent
Larsen et al.

(10) Patent No.: US 11,737,698 B2
(45) Date of Patent: Aug. 29, 2023

(54) SYSTEM AND METHOD FOR PROCESSING ELECTROPHYSIOLOGICAL SIGNALS

(71) Applicant: CathVision ApS, Copenhagen N (DK)

(72) Inventors: Sigge Nejst Larsen, Copenhagen N (DK); Victor Shadbolt, Ancaster (CA); David P. MacAdam, Millbury, MA (US); Harold Wodlinger, Thornhill (CA)

(73) Assignee: CathVision ApS, Copenhagen N (DK)

( * ) Notice: Subject to any disclaimer, the term of this patent is extended or adjusted under 35 U.S.C. 154(b) by 112 days.

(21) Appl. No.: 16/979,792

(22) PCT Filed: Mar. 12, 2019

(86) PCT No.: PCT/EP2019/056136
§ 371 (c)(1),
(2) Date: Sep. 10, 2020

(87) PCT Pub. No.: WO2019/175156
PCT Pub. Date: Sep. 19, 2019

(65) Prior Publication Data
US 2021/0038103 A1      Feb. 11, 2021

Related U.S. Application Data

(60) Provisional application No. 62/642,325, filed on Mar. 13, 2018.

(51) Int. Cl.
*A61B 5/30*     (2021.01)
*A61B 5/287*    (2021.01)
*H03M 1/18*     (2006.01)

(52) U.S. Cl.
CPC ............... *A61B 5/30* (2021.01); *A61B 5/287* (2021.01); *H03M 1/18* (2013.01)

(58) Field of Classification Search
CPC ................................. A61B 5/30; A61B 5/287
(Continued)

(56) References Cited

U.S. PATENT DOCUMENTS 5,458,621 A      10/1995   White
2008/0004536 A1*  1/2008   Baxi ..................... A61B 5/304
                                                      600/509

(Continued)

OTHER PUBLICATIONS

International Search Report and Written Opinion of International Searching Authority for Application No. PCT/EP2019/056136, dated Jun. 3, 2019 (12 pages).

*Primary Examiner* — Nicole F Lavert
(74) *Attorney, Agent, or Firm* — NIXON PEABODY LLP

(57) ABSTRACT

An electrophysiology system including signal channels each of which processes an electrophysiological signal along a signal path extending from an input port that receives the analog electrophysiological signal, via an adjustable gain element that amplifies the electrophysiological signal, and via an ADC element that converts the analog signal into a corresponding digital signal, to an output port. The system further includes a monitoring element that generates a monitoring signal representative of a DC component of the electrophysiological signal and a gain control element that generates a control signal responsive to the monitoring signal. The control signal controls the gain setting of the gain element to cause a decrease in gain, if an increase in the magnitude of the DC component is determined; and/or an increase in gain, if a decrease in the magnitude of the DC component is determined.

17 Claims, 2 Drawing Sheets

(58) Field of Classification Search
USPC .................................................. 600/508–509
See application file for complete search history.

(56) References Cited

U.S. PATENT DOCUMENTS

| 2015/0005585 A1 | 1/2015 | Xu |
| 2015/0223758 A1 | 8/2015 | Park |
| 2018/0042526 A1* | 2/2018 | Hong .................... A61B 5/7455 |

* cited by examiner

SYSTEM AND METHOD FOR PROCESSING ELECTROPHYSIOLOGICAL SIGNALS

CROSS-REFERENCE TO RELATED APPLICATIONS

This application is a U.S. National Stage of International Application No. PCT/EP2019/056136, filed Mar. 12, 2019, which claims the benefit of U.S. Provisional Application No. 62/642,325, filed Mar. 13, 2018, both of which are incorporated herein by reference in their entireties.

TECHNICAL FIELD

The present invention relates in one aspect to an electrophysiology system comprising one or more signal channels for recording electrophysiological signals, such as cardiac signals, in particular intracardiac signals, wherein each signal channel is adapted for processing an electrophysiological signal along a signal path extending from an input port configured for receiving the electrophysiological signal as an analog signal, via at least one gain element adapted for amplifying the electrophysiological signal, and via an ADC element adapted for converting the analog signal into a digital signal corresponding to the electrophysiological signal, to an output port arranged for providing the digital signal as an output. According to a further aspect, the electrophysiology system further comprises devices for applying cardiac pacing, intracardiac ablation, and/or defibrillation. According to a particular aspect, the electrophysiological system is adapted for processing, displaying, and/or recording intracardiac electrophysiological signals in combination with applying cardiac pacing, intracardiac ablation, and/or defibrillation. According to a yet further aspect, the electrophysiological system is adapted for use in intracardiac electrophysiology procedures.

BACKGROUND OF THE INVENTION

In intracardiac electrophysiology procedures, several catheters are inserted into the heart through the femoral vein in order to diagnose and treat cardiac arrhythmias. Each of these catheters has multiple electrodes at their distal end. Electrodes are used to record electrical signals, pace the heart using voltage or current pulses, and ablate cardiac tissue using radio-frequency voltages.

The electrophysiological signals are the observation of corresponding electrophysiological potentials as a function of time. Accordingly, intracardiac (electrophysiological) signals are the observation of corresponding intracardiac (electrophysiological) potentials as a function of time. The electrodes may be used for picking up an electrophysiological potential at the respective location of the electrodes. The electrophysiological potentials may be passed via electrical conductors from the distal end of the catheter to a connector interface at the proximal end of the catheter, and further to recording equipment for amplification, processing, display and storage of signals representative of the electrophysiological potentials. The intracardiac electrophysiological signals may e.g. be measured by amplifying the potential difference between a first terminal and a second terminal, wherein at least the first terminal is connected to an electrode that is placed inside the heart. The second terminal may be configured as a reference terminal for providing an electrophysiological reference. The obtained intracardiac signals may be further amplified/processed and/or digitized for noise reduction in the analog and/or digital domain, for display on a computer, and/or for storage on a digital storage medium.

By recording/mapping a plurality of electrophysiological signals from signal electrodes placed inside the heart, details about a pathological state relating to cardiac arrhythmia in an individual can be obtained and proper treatment, such as an ablation treatment, can be developed. The aspects of the recorded intracardiac signals to be studied include the presence or absence of characteristic features in a given signal, the periodicity and regularity of repetition of the signals, as well as the amplitude and morphology of the signals. At least some types of electrophysiology procedures may also involve pacing stimulation of the heart. Furthermore, defibrillation of the heart may be required.

Radiofrequency catheter ablation procedures may e.g. be indicated for cases of atrial fibrillation, recurrent atrial flutter, atrial tachycardia, multifocal atrial tachycardia, supraventricular tachycardia, and ventricular arrhythmia. The energy-emitting probe (electrode) is located at the distal end of a catheter which is placed into the heart. The relevant intracardiac locations to be scarred may be identified in a mapping operation identifying regions of abnormal electrical activity. Once the relevant tissue has been identified, an ablation procedure is performed typically involving the "drawing-up" point-by-point one or more scar lines of ablated tissue.

A high quality recording of intracardiac electrophysiological signals both prior to and during an actual ablation is therefore important for the treatment to succeed. Furthermore, a high quality recording of intracardiac electrophysiological signals is also important immediately after an ablation has been performed, not the least for confirming the correct treatment.

Catheter electrodes may be connected to electrophysiology amplifiers, which amplify and record signals, cardiac stimulators, which provide pacing pulses, and ablation machines, at the same time. One of the most important characteristics of an electrophysiology amplifier is thus the fidelity of its signal amplification and recording, including the morphology of the signals. In particular, electrical noise must be minimized. Amongst others, an electrophysiology amplifier stage used in a system for intracardiac procedures has to be robust against interference signals, such as stemming from transients generated by any of the above-mentioned equipment for intracardiac electrophysiology procedures, i.e. ablation, pacing, or even defibrillation. Furthermore, a fast recovery from the effect of transient interference signals is of the utmost importance in order to allow for a prompt and direct patient monitoring during intracardiac procedures.

Modern electrophysiology amplifiers have an analog first stage (front end) followed by an analog-to-digital converter (ADC). The electrical noise generated by the ADC is inversely proportional to its internal gain. To minimize electrical noise, therefore, the gain of the ADC should be maximized. However, this is not generally possible because a second requirement for electrophysiology amplifiers is the ability to recover quickly from an overload caused by pacing pulses, ablation, or defibrillation pulses. Recovery time is minimized by amplifying the signal over a wide bandwidth that includes DC. DC coupling limits the gain that can be used in the ADC because the DC amplitude (DC offset) is typically much larger than the AC amplitude of cardiac signals, so too much gain would cause the ADC to saturate, resulting in the loss of the signal. Furthermore, the DC offset typically increases during cardiac pacing and especially during ablation, and this increase in DC offset can be very significant. Therefore, electrophysiology amplifiers common in the art either have low ADC gain, resulting in undesirable levels of electrical noise, or are AC coupled, resulting in long recovery time after pacing and defibrillation.

Therefore, there is a need for an improved electrophysiology system for intracardiac procedures, which provides high fidelity intracardiac electrophysiological signals with improved noise performance, yet providing a fast recovery after transient interferences. One object of the present invention is therefore to provide such improvements to electrophysiology systems for intracardiac procedures.

SUMMARY OF THE INVENTION

The present invention addresses these issues by automatically adjusting the gain inversely in proportion to a DC component of the signal. To that end, the DC offsets on one or more of the intracardiac electrodes connected to the system are determined, and the gain of the ADC is adjusted by implementing one or more of the embodiments described below. Typically, according to preferred embodiments at least the gain of an ADC element is adjusted in proportion to the measured DC component of the signal. Furthermore, according to some embodiments, the gain is adjusted stepwise, wherein the gain steps are developed in a digitized manner inversely in proportion to the measured DC component of the signal.

The object of the present invention is achieved by the embodiments as defined by the appended claims and as disclosed herein in the following.

A first aspect of the invention relates to an electrophysiology system comprising one or more signal channels, wherein each signal channel is adapted for processing an electrophysiological signal along a signal path extending from an input port configured for receiving the electrophysiological signal as an analog signal, via at least one adjustable gain element adapted for amplifying the electrophysiological signal with a gain according to a gain setting, and via an ADC element adapted for converting the analog signal into a digital signal corresponding to the electrophysiological signal, to an output port adapted for providing the digital signal as an output; wherein the electrophysiology system further comprises: a monitoring element configured for generating a monitoring signal representative of a magnitude of a DC component of the electrophysiological signal; and a gain control element configured for generating a control signal in response to the monitoring signal, wherein the control signal is adapted to control the gain setting of the adjustable gain element so as to cause a decrease in gain if an increase in the magnitude of the DC component is determined; and/or an increase in gain if a decrease in the magnitude of the DC component is determined.

The signal path extends from an upstream end at the input port in a downstream direction to a downstream end at the output port and thus defines a direction of a processing flow for the intracardiac signal. At the upstream end, the electrophysiological signal is received with any low frequency components including DC components. Most preferably, the signal path does not contain low frequency filtering, i.e. at least not to a significant level, prior to converting the analog signal into a digital signal. Thereby, an aggressive filtering is avoided that otherwise might cause signal distortion and/or might extend signal recovery time beyond a pre-defined maximum value. Appropriate DC suppression filtering may then subsequently be applied at the downstream end of the signal path, in the digital domain, in particular for the purpose of generating a display signal for presentation on a signal display and/or for the purpose of generating a recording signal for storage in a signal recorder. The ADC element is for converting the electrophysiological signal into the digital domain. The digital signal representing the electrophysiological signal is then presented at the output port as an output. The digital signal may further be processed for purposes of displaying, analyzing, and/or storing data representing the intracardiac signal.

The monitoring element is for monitoring the electrophysiological signal in the signal channel and for generating a monitoring signal representative of a magnitude of at least a DC component of the electrophysiological signal, or of a low frequency component indicative of the DC component, of the electrophysiological signal. Generating the monitoring signal may employ any suitable measurement and/or data analysis technique for determining a quantity representative of a DC component (or slowly varying signal component) of the electrophysiological signal. The monitoring signal is passed to the gain control element for generating a control signal in response to the monitoring signal. The control signal is then passed to the adjustable gain element for setting the gain. The term adjustable gain element as used herein refers to a gain element comprising circuitry that allows for adjusting the gain according to a gain setting in response to a control signal applied thereto.

The control signal is configured such that the gain is adjusted inversely of the determined magnitude of the DC component (or slowly varying background component) of the electrophysiological signal. Gain adjustment is preferably made according to a pre-defined scheme. For example, gain adjustment may be performed stepwise with gain settings according to pre-determined magnitude ranges for the DC component, and/or with gain settings according to pre-determined threshold values for changes in the magnitude of the DC component.

The system automatically determines the DC component of the collected electrophysiological signal and adjusts the ADC gain to obtain an optimum compromise for the noise performance, or at least an improved noise performance. The above-discussed issues relating to the build-up of a large DC component during e.g. intracardiac procedures are thus mitigated. For example, when ablation is activated, the DC component of an intracardiac signal typically slowly increases, and when ablation is deactivated, the DC component returns to normal. During a diagnostic phase of the electrophysiology procedure, when signal fidelity is most crucial, the DC component is generally low, so the ADC gain can be set to a relatively high value, minimizing the electrical noise and providing signal fidelity that exceeds systems known in the art. During ablation, the DC component gradually increases, and the system responds by gradually lowering the ADC gain. This typically results in an increase in electrical noise. However, this level of noise will never increase beyond that of a fixed gain system as known in the art. When the ablation is stopped, the DC component will again decrease in magnitude, and the system will restore the higher gain setting, resulting in improved signal fidelity.

Further according to some embodiments, the electrophysiology system comprises an electrophysiology amplifier portion, the electrophysiology amplifier portion comprising: a front end; and the ADC element. The front end of the electrophysiology amplifier portion is for receiving and amplifying the analog electrophysiological signals from e.g. electrodes of intracardiac catheters connected to the amplifier portion. The amplified signals are then passed to the ADC where the analog signals are digitized, and the digitized signal is provided as an output for subsequent processing, such as filtering, display, and/or storage. The signal path therefore comprises at least a first gain element in the front end, and typically further comprises a second gain element in the ADC. The gain of the first gain element and the gain of the second gain element may both be adjustable according to a gain setting in response to a control signal.

Further according to some embodiments, the electrophysiology system further comprises a computer portion, the computer portion comprising a processor with programmed instructions for implementing at least a software instance of the monitoring element; and a software instance of the gain control element. The magnitude of the DC component may thus be determined by analyzing the intracardiac signal in the digital domain, and a corresponding control signal is developed based on the result of this analysis. Preferably, both the monitoring element and the gain control element are therefore implemented in a computer portion as software instances. A first module for implementing the monitoring element is configured for receiving the digital data representing the electrophysiological signal, analyzing the digital data with respect to a DC component of the electrophysiological signal, and deriving a monitoring signal indicative of a magnitude of the DC component. The monitoring signal is passed to a second module implementing the gain control element. The second module is configured for receiving the monitoring signal indicative of a magnitude of the DC component of the electrophysiological signal and develops a gain control signal based on the monitoring signal, e.g. according to a pre-determined scheme. The control signal is then passed to the relevant adjustable gain element or gain elements, e.g. in the form of a digital gain setting instruction. An electrophysiology system using computer implemented analysis and control is fast and flexible, and can easily be reconfigured according to the constraints and specifications of a particular electrophysiology set-up.

Further according to some embodiments, the electrophysiology system comprises firmware adapted to implement a firmware instance of the monitoring element and a firmware instance of the gain control element. Preferably, the firmware is arranged in the electrophysiology amplifier portion. The firmware is adapted for determining a DC component and control of the gain setting in the same manner as discussed above. Essentially, the same functions are performed, but there is no need for an external computer. Furthermore, the output of the firmware can be adapted for driving a signal display directly as a failsafe mechanism in case of computer failure, without compromising on the improved noise performance achieved by the present invention.

The DC component may thus be determined using a digital filter either in software instances or in firmware instances. Advantageously according to another embodiment, a DC component may also be determined using an analog filter and a comparator within the electrophysiology amplifier portion. This allows for making the software or firmware less complex and use less memory.

Further according to some embodiments, the electrophysiology system further comprises an output data generator element configured for receiving the digital signal from the ADC element as an input; and processing the digital signal so as to produce output data adapted for display and/or storage. The output data are useful e.g. for presentation on a signal display or for recording in a data storage.

Typically, the signal display is configured to produce a graphical representation of the intracardiac signal based on the output data.

Further according to some embodiments of the electrophysiology system, processing the digital signal so as to produce output data includes scaling of the amplitude of the output data in response to the control signal from the gain control element, in particular so as to compensate for changes in gain in the adjustable gain element). As mentioned above, the gain control element passes a control signal, e.g. in the form of a digital gain setting instruction, back to the gain element, such as the gain element of the ADC and the gain is adjusted accordingly. At the same time, the gain setting instruction is sent to an output data generator, such as a module for the generation of display data, which uses the gain setting instruction to adjust the displayed signal amplitude.

If the gain of the ADC is adjusted without a corresponding adjustment in the display of the signal by the computer, then the signal amplitude displayed by the computer will also appear to change. Since the signal amplitude does not actually change, the display parameters must be adjusted simultaneously with the gain adjustment. Furthermore, the display data is also filtered so that slow changes in DC offset are not visible. The display data is thus scaled in response to the control signal from the gain control element so as to compensate for (any) changes in gain applied to the electrophysiological signal upstream of the display data generator.

The display signal amplitude may be scaled with a display gain factor, wherein the display gain factor is increased so as to compensate for a decrease in converter gain, and the display gain factor is decreased so as to compensate for an increase in converter gain. The signal is thus displayed invariant with respect to gain changes. Advantageously, digital processing may further include removal of a DC component in order to present the output data representing intracardiac signals with a constant baseline. Also, further filtering and signal analysis may be applied. Consequently, output data may be presented to the user, which enables the user to more directly and rapidly respond to any changes picked up by the intracardiac electrodes, thereby improving the precision of the user's interaction with the electrophysiology system. In particular, this improves patient safety.

Further according to some embodiments of the electrophysiology system, the adjustable gain element is an adjustable ADC gain element arranged in the ADC element. By providing the ADC element with an adjustable gain element, the internal gain of the ADC element can be adjusted automatically in response to the control signal so as to automatically optimize the overall noise performance according to the monitored DC component of the electrophysiological signal. The adjustable ADC gain element may be part of an integrated circuitry, which may be configured in response to digital instructions so as to change the gain setting. The control signal may in this case be provided in the form of a suitable digital instruction. Instructing an ADC element with an integrated adjustable gain element may require halting the ADC element temporarily to perform the gain change.

Further according to some embodiments of the electrophysiology system according to any of the preceding claims, wherein the adjustable gain element is an adjustable front end gain element arranged in an analog front end arranged upstream of the ADC element. By providing the front end with an adjustable front end gain element, the gain of the front end arranged upstream of the ADC element can be adjusted automatically in response to the control signal so as to automatically optimize the overall noise performance according to the monitored DC component of the electrophysiological signal. As for the adjustable ADC gain element, the gain of the adjustable front end gain element could be adjusted automatically, either by software, firmware, or analog processing as described above. Changing the gain of a front end gain element may e.g. be accomplished by changing resistor values using analog switches, and this would not require the ADC to be halted.

Further according to some embodiments of the electrophysiology system, each signal channel comprises at least two adjustable gain elements. The two adjustable gain elements may be operated in combination to adjust the overall gain of the electrophysiology system in response to the monitored DC component so as to automatically optimize the noise performance using any of the techniques as described herein. For example, the system may comprise both an adjustable front end gain element, such as with an analog gain adjustment circuitry, and an adjustable ADC gain element, such as with a digital configuration logics.

Advantageously according to some embodiments of the electrophysiology system, a first gain element is an ADC gain element arranged in the ADC element. Further advantageously according to some embodiments of the electrophysiology system, a second gain element is a front end gain element arranged in an analog front end arranged upstream of the ADC. The gain settings for first and second gain elements may be controlled by respective first and second control signals generated by the control unit in response to the monitoring signal. The first and second control signals may be different or may be the same.

Further according to some embodiments of the electrophysiology system, the monitoring element is configured for monitoring the electrophysiological signals of a plurality of signal channels.

Further according to some embodiments of the electrophysiology system, the monitoring element is further configured for determining the magnitude of the largest DC component of the monitored electrophysiological signals, wherein the monitoring signal is representative of the magnitude of said largest DC component. Thereby an overall compromise of the noise performance is achieved that ensures signal integrity for all monitored channels.

Further according to some embodiments of the electrophysiology system, the monitoring element is configured for generating a monitoring signal for a selected signal channel in lieu of a group of signal channels. The monitoring element is thus configured for monitoring a selected signal channel in lieu of a group of signal channels and for generating a monitoring signal representative of a magnitude of at least a DC component (or low frequency component) of an electrophysiological signal in the selected signal channel in lieu of the magnitude of the DC components of the electrophysiological signals in each of a group of signal channels.

Advantageously according to some embodiments of the electrophysiology system, at least one of the signal channels is configured as an ablation channel adapted for collecting intracardiac electrophysiological signals from an intracardiac ablation electrode. The ablation channel is thus adapted to collect signals from an intracardiac electrode connected to the ablation channel during an ablation procedure, i.e. also when ablation energy is applied to cardiac tissue through the ablation electrode. Preferably, the above-mentioned selected signal channel is configured as an ablation channel. In an ablation procedure, the DC component may thus be determined solely for the signal channel connected to the ablation electrode. Since the ablation electrode usually has the largest DC offset, measuring on this electrode alone would still be effective for optimizing/improving the noise performance in an automatic manner, but would be far less costly than solutions monitoring multiple or all electrodes involved in such a procedure.

Further according to some embodiments, the electrophysiology system comprises a plurality of ADC elements and associated gain elements; wherein each of the ADC elements and associated gain elements is dedicated to a respective group of signal channels; and wherein the gain control element is configured for adjusting the gain of each of the associated gain elements according to DC components of electrophysiological signals in one or more of the signal channels of the respective group.

A respective monitoring signal is generated for each of the groups. The monitoring signals for a group represent a magnitude of DC components (or low frequency component) observed in one or more of the signal channels in that group. Monitoring signals are generated for each of the groups and corresponding control signals are then generated for each of the groups of signal channels based on the respective monitoring signals. The control signals are then used for adjusting the respective gain of the respective gain elements.

Several ADC elements are thus used, each one dedicated to a particular group of electrodes. Each ADC may have its gain adjusted automatically according to the determined DC component of one or more electrophysiological signals from of its group of electrodes. Thereby signal fidelity is maximized or at least improved for the majority of electrodes, assuming that only a minority of electrodes exhibit high DC offset. Preferably in these embodiments, display of the signals is also controlled for the signals corresponding to each ADC so as to compensate for any changes in gain.

Further according to some embodiments, the electrophysiology system comprises at least one signal channel with a first signal path comprising a first ADC element and an associated first gain element, and a second signal path comprising a second ADC element with an associated second gain element, the first and second signal paths being arranged in parallel, wherein both the first and second signal paths are configured for receiving, amplifying, and converting the same analog electrophysiological signal into first and second digital signals corresponding to the electrophysiological signal, respectively; and wherein the system is configured to only apply changes to gain and/or ADC settings in the first signal path when the second digital signal is provided as the output; and to only apply changes to gain and/or ADC settings in the second signal path when the first digital signal is provided as the output.

A drawback of embodiments using an ADC integrated gain element that is digitally configured as described above is that such ADCs typically must be halted in order to change their gain. This results in the loss of data during the period where the ADC is halted. In some applications, the loss of data, even for a very short time period, is not acceptable. This can thus be addressed by feeding the analog data to two ADCs in parallel. A subsequent computer initially accepts data from the first ADC. If the DC offset changes such that the gain needs to be adjusted, the computer programs the second ADC with the adjusted gain without stopping the first ADC. Once the second ADC has started, the computer accepts data from the second ADC with no loss of data. The roles are then reversed: any change in DC offset results in a new gain for the first ADC, and the computer then accepts data from this first ADC without losing data. This embodiment is typically more expensive, because it requires double the number of ADCs and significantly more processing in software. However, any loss of data or other signal artefacts related to the halting may thereby be completely avoided.

Advantageously according to some embodiments, the electrophysiology system further comprises devices for applying cardiac pacing, intracardiac ablation, and/or defibrillation. According to a particular aspect, the electrophysiological system is adapted for processing, displaying, and/or recording intracardiac electrophysiological signals in combination with applying cardiac pacing, intracardiac ablation, and/or defibrillation. According to a yet further aspect, the electrophysiological system is adapted for use in intracardiac electrophysiology procedures.

Further advantageously according to some embodiments, the electrophysiology system further comprises one or more intracardiac catheters adapted for use in minimally invasive intracardiac procedures, each catheter comprising at a distal end thereof one or more electrodes, preferably a plurality of electrodes, the electrodes being connected to corresponding input ports of the signal channels for the observation of intracardiac signals. Furthermore, the electrodes may include any electrodes particularly adapted for certain intracardiac procedures, such as ablation electrodes for ablation procedures, pacing electrodes for applying cardiac stimulation pulses there through, and electrodes suitable for any combination of intracardiac applications.

A further aspect of the invention relates to a method of amplifying an electrophysiological signal in a signal channel, wherein the method comprises the steps of:
  receiving the electrophysiological signal as an analog signal;
  amplifying the electrophysiological signal with a gain according to a gain setting;
  converting the analog signal into a digital signal corresponding to the electrophysiological signal;
  monitoring the electrophysiological signal to obtain a magnitude of at least a DC component of the electrophysiological signal;
  controlling the gain setting of the adjustable gain element in response to the magnitude of the DC component; and
  providing the digital signal as an output.

In particular, the gain setting of the adjustable gain element is controlled such that the gain changes inversely in response to the magnitude of the DC component. Controlling the gain setting is thus configured to cause a decrease in gain if an increase in the magnitude of the DC component is determined; and/or an increase in gain if a decrease in the magnitude of the DC component is determined. Controlling may be performed stepwise according to a pre-determined switching scheme depending on the magnitude of the DC component.

Further advantageous embodiments of the method may include any further steps as also required for operating any of the advantageous embodiments of the electrophysiology system as disclosed herein, whereby the corresponding advantages are achieved.

BRIEF DESCRIPTION OF THE DRAWINGS

Preferred embodiments of the invention will be described in more detail in connection with the appended drawings, which show in FIG. 1 a simplified block diagram of an electrophysiology system according to one embodiment; and in FIG. 2 a composite graph showing schematically from bottom to top: an ablation signal, an intracardiac signal amplitude, a gain, and a display signal amplitude.

DETAILED DESCRIPTION

Figure 1:
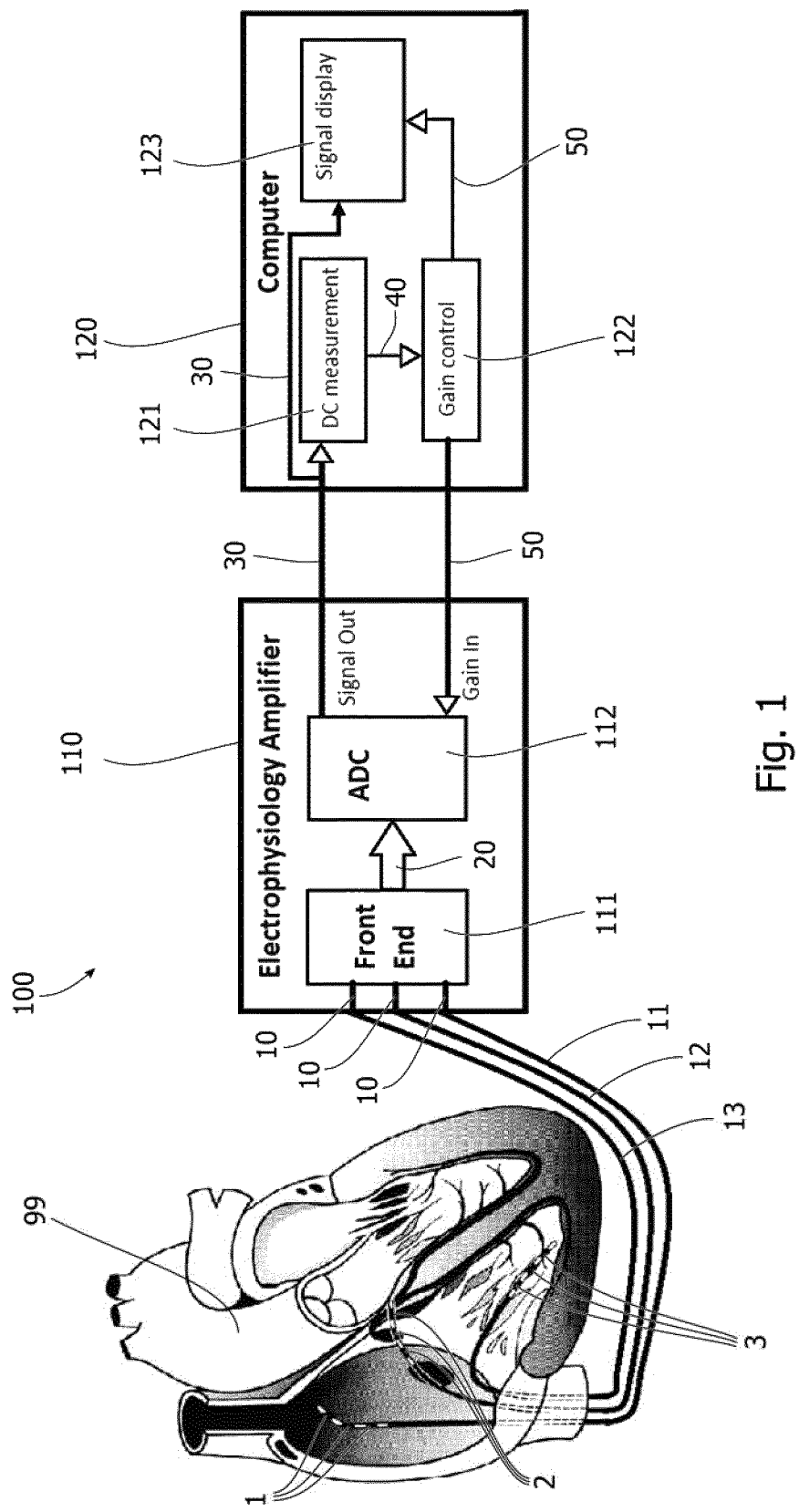

FIG. 1 shows a simplified block diagram of an electrophysiology system 100 according to one embodiment of the invention. The system 100 comprises an electrophysiology amplifier portion 110 with a front end 111 and an ADC element 112, and a computer portion 120 configured for digital signal processing and/or display. Preferably, as shown in FIG. 1, a measurement of the DC component and the subsequent gain control of the gain are performed in software instances 121, 122 implemented in the computer 120. The computer 120 is further configured to display data representing the intracardiac signal on a signal display module 123. Preferably, as also shown in FIG. 1, the signal display is scaled according to information 50 from the gain control 122 so as to render the displayed signal invariant with respect to gain changes.

The front end 111 of the electrophysiology amplifier portion is for receiving and amplifying primary analog intracardiac signals 10 from electrodes 1, 2, 3 of intracardiac catheters 11, 12, 13 connected to the amplifier portion 110. Schematically in FIG. 1, three catheters 11, 12, 13 are shown inside the heart 99 in various positions. Catheter electrodes 1, 2, 3 are shown as black stripes at the distal end of the catheters 11, 12, 13. The electrodes 1, 2, 3 are connected to the front end 111 of the electrophysiology amplifier 110. The front end 111 may or may not include an amplifier. The front end 111 may further include defibrillator protection and low-pass filters for anti-aliasing or rejection of ablation or localization signals, notch filters to reject powerline frequencies, and/or buffers. The primary analog signals 10 are passed through the front end to provide secondary analog signals 20, which are passed to the ADC 112 where the secondary analog signals 20 are digitized to provide digital signals 30 representing the intracardiac signals. The output 30 of the ADC 112 is sent to a computer 120. The software in the computer is shown schematically as three blocks 121, 122, 123. The first block 121 (DC measurement) analyzes all of the signals 30 and calculates the largest DC component on any electrode 1, 2, 3. This information is passed as a monitoring signal 40 to the gain control block 122. The gain control block 122 sends a digital instruction 50 back to the ADC 112 that adjusts its gain. At the same time, the gain instruction 50 is sent to the signal display block 123, which uses the gain instruction 50 to adjust the displayed signal amplitude so as to render the signal display invariant with respect to gain changes.

Figure 2:
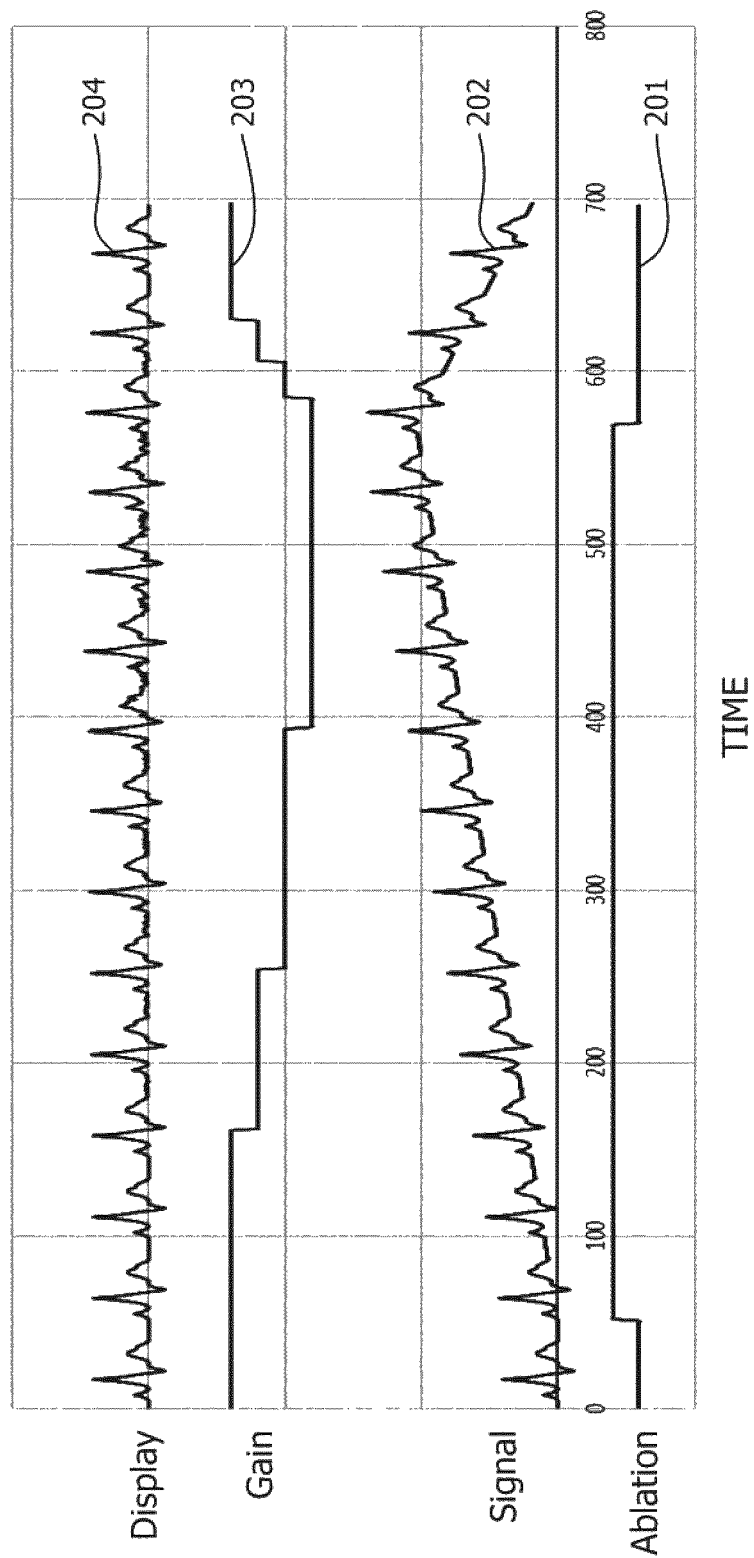

FIG. 2 shows the signal flow in a schematic composite graph with a binary (on/off) ablation control signal 201 ("Ablation") indicating the presence of ablation energy applied through an intracardiac ablation electrode, an intracardiac signal amplitude 202 ("Signal"), a gain setting 203 ("Gain"), and a display signal amplitude 204 ("Display") on the co-ordinate axes over time on the ordinate axis. While the signal 204 is labelled as a "display" signal, it generally represents by way of example digital output data 204 that may equally be considered as a recorded signal for storage or any further subsequent analysis.

Ablation 201 turns on at time '50' and turns off at time '570'. When ablation 201 is activated, the DC component of the intracardiac signal 202 slowly increases, and when ablation 201 is deactivated, the DC component of the intracardiac signal 202 returns to normal. If the DC component gets too large, the ADC may be driven into saturation and lose the signal 202. To avoid that, the system automatically measures the DC component and reduces the ADC gain 203 in steps. When the DC component is reduced after ablation 201 is deactivated, the gain 203 is increased back to the original level. A displayed signal 204 is invariant with respect to changes in the gain 203, since the change in ADC gain 203 is compensated by the computer as discussed above. Furthermore, the displayed signal 204 does not drift on the screen because the DC component is filtered out. Noise in the displayed signal 204 is a maximum when the DC component is a maximum and the ADC gain is lowest. The noise in this region corresponds to the noise of a fixed gain system also when no ablation is applied. However, as also seen in FIG. 2, noise in the displayed signal 204 is notably reduced in regions of lower DC-offset in an automatic manner.

In addition to the operation of the electrophysiology system as described above, further advantageous variations of the above embodiment may be conceived. The skilled person may conceive that these embodiments are also included in the scope of the present invention. For example, measurement of the DC component and control of the ADC gain may be performed in firmware, entirely within the electrophysiology amplifier portion 110, wherein all of the same functions are performed, but where there is no need for an external computer 120. This embodiment has the advantage that the electrophysiology amplifier 110 could drive a signal display directly as a failsafe mechanism in case of computer failure.

Furthermore in variation of the above-described embodiments, where the DC components of the intracardiac signals are measured for all electrodes, and the largest offset is used to adjust the gain, a representative DC component may be measured solely on the signal channel connected to an ablation electrode in lieu of the remaining signal channels. Since the ablation electrode usually has the largest DC offset, measuring on the intracardiac signal from this electrode alone would still be effective but would be far less costly.

In a further variation of the above described embodiments, a DC offset component may also be measured using an analog filter and a comparator within the electrophysiology amplifier 110. This allows for a software or firmware that is less complex and uses less memory.

In yet another variation of the above-described embodiment, several ADCs may be used in the ADC block 112, each one dedicated to a particular group of electrodes. Each of the several ADCs may have its gain adjusted automatically by measuring the DC component of one or more intracardiac signals of its group of electrodes. This embodiment maximizes signal fidelity from the majority of electrodes, assuming that only a minority of electrodes exhibit high DC offset. In this embodiment, display of the signals on the signal display 123 would advantageously also be controlled for the signals corresponding to each of the several ADCs.

A reconfiguration of the internal gain of an ADC by digital instructions typically requires that the ADC must be halted in order to change the gain. This results in the loss of data during the period where the ADC is halted. In some applications, the loss of data, even for a very short time period, is not acceptable. In a yet further variation of the above embodiments, this can be addressed by feeding the analog data to two ADCs arranged in the ADC block 112 in parallel. The computer 120 initially accepts data from the first ADC. If the DC offset changes such that the gain needs to be adjusted, the computer 120 programs the second ADC with the adjusted gain without stopping the first ADC. Once the second ADC has started, the computer accepts data from the second ADC with no loss of data. The roles are then reversed: any change in DC offset results in a new gain for the first ADC, and the computer 120 then accepts data from this first ADC without losing data. This embodiment is more expensive because it requires double the number of ADCs and significantly more processing in software, but it completely avoids any loss of data or other signal artefacts. In certain electrophysiology amplifier designs, the noise generated by the front end (pre-amplifier or input stage) may also depend on its gain setting.

In a yet further variation of the above embodiment, the gain of the front end could be adjusted automatically in response to a control signal 50, either by software, firmware, or analog filter as described above. Changing the gain of the front end may advantageously be accomplished using analogy circuitry, e.g. by changing resistor values using analog switches. This has the advantage that it does not require the ADC to be halted in order to automatically adapt the gain configuration for applying a dynamic optimization of the noise performance.

Finally, both the front end gain and the ADC gain could be automatically adjusted in combination using any of the techniques described above.

Generally, the present invention as disclosed herein is particularly useful for applications requiring the processing of intracardiac signals, especially in the context of intracardiac electrophysiological procedures, such as intracardiac ablation. However, the invention may also be useful more generally for any application that requires a very low noise digitized signal in an environment where there are varying DC offsets that can become large as compared to the signal of interest. In particular, the present invention is useful where a small AC signal tends to be masked by a baseline drift, but where removal of the DC-component would distort or otherwise affect/compromise the signal of interest and/or where removal of said DC-component by filtering, e.g. using an AC-coupling at the inputs of the system, would cause an unacceptable slow recovery after removal of the cause of the DC-offset. For example, the system and method for processing electrophysiological signals may also be useful in the context of electroencephalography (EEG) and other electrophysiological signals.

The invention claimed is:

1. Electrophysiology system comprising:
   one or more signal channels, wherein at least one signal channel is configured to process an electrophysiological signal, which includes intracardiac ablation energy, along a signal path extending from an input port configured to receive the electrophysiological signal as an analog signal, via at least one adjustable gain element configured to amplify the electrophysiological signal with a gain according to a gain setting, and via an analog-to-digital (ADC) element configured to convert the analog signal into a digital signal corresponding to the electrophysiological signal, to an output port configured to provide the digital signal as an output;
   a monitoring element configured to generate a monitoring signal representative of a magnitude of a DC component of the electrophysiological signal;
   a gain control element configured to generate a control signal in response to the monitoring signal, wherein the control signal is configured to control the gain setting of the adjustable gain element so as to cause a decrease in gain in response to an increase in the magnitude of the DC component caused by activation of the intracardiac ablation energy; and/or an increase in gain in response to a decrease in the magnitude of the DC component caused by deactivation of the intracardiac ablation energy.

2. Electrophysiology system according to claim 1, further comprising an electrophysiology amplifier portion having a front end and the ADC element.

3. Electrophysiology system according to claim 1, further comprising a computer portion, the computer portion including a processor with programmed instructions for implementing:
a software instance of the monitoring element; and
a software instance of the gain control element.

4. Electrophysiology system according to claim 1, further comprising firmware configured to implement:
a firmware instance of the monitoring element; and
a firmware instance of the gain control element.

5. Electrophysiology system according to claim 1, further comprising an output data generator element configured to:
receiving the digital signal from the ADC element as an input; and
processing the digital signal so as to produce output data adapted for display and/or storage.

6. Electrophysiology system according to claim 5, wherein the processing the digital signal includes scaling of the amplitude of the output data in response to the control signal from the gain control element.

7. Electrophysiology system according to claim 1, wherein the adjustable gain element is an adjustable ADC gain element arranged in the ADC element.

8. Electrophysiology system according to claim 1, wherein the adjustable gain element is an adjustable front end gain element arranged in an analog front end arranged upstream of the ADC element.

9. Electrophysiology system according to claim 1, wherein each of the signal channels includes at least two adjustable gain elements.

10. Electrophysiology system according to claim 1, wherein the monitoring element is configured for monitoring the electrophysiological signal of a plurality of signal channels.

11. Electrophysiology system according to claim 1, wherein the monitoring element is further configured for monitoring the magnitude of a largest DC component of the at least one electrophysiological signal that includes ablation energy to provide a wherein the monitoring signal representative of the magnitude of said largest DC component.

12. Electrophysiology system according to claim 1, wherein the monitoring element is configured for generating a monitoring signal for a selected signal channel in lieu of a group of signal channels.

13. Electrophysiology system according to claim 1,
wherein the system comprises a plurality of ADC elements and associated gain elements;
wherein each of the ADC elements and associated gain elements is dedicated to a respective group of signal channels; and
wherein the gain control element is configured for adjusting the gain of each of the associated gain elements according to DC components of intracardiac signals in one or more of the signal channels of the respective group.

14. Electrophysiology system according to claim 1, wherein at least one of the signal channels has a first signal path including a first ADC element and an associated first gain element, and a second signal path including a second ADC element with an associated second gain element, the first and second signal paths being arranged in parallel, wherein both the first and second signal paths are configured for receiving, amplifying, and converting the same analog intracardiac signal into first and second digital signals corresponding to the intracardiac signal, respectively; and wherein the system is configured
to only apply changes to gain and/or ADC settings in the first signal path when the second digital signal is provided as the output; and
to only apply changes to gain and/or ADC settings in the second signal path when the first digital signal is provided as the output.

15. Electrophysiology system according to claim 1, wherein the intracardiac ablation energy is provided by an intracardiac ablation electrode.

16. Method of amplifying an electrophysiological signal in a signal channel, the method comprising the steps of:
receiving the electrophysiological signal as an analog signal;
amplifying the electrophysiological signal during a diagnostic phase and signal with a gain according to a gain setting;
converting the analog signal into a digital signal corresponding to the electrophysiological signal;
monitoring the electrophysiological signal to obtain a magnitude of a DC component of the electrophysiological signal;
controlling the gain setting of the adjustable gain element in response to: an increase of the magnitude of the DC component by activation of intracardiac ablation energy, and a decrease of the magnitude of the DC component by deactivation of the intracardiac ablation energy; and
providing the digital signal as an output.

17. Electrophysiology system comprising:
one or more signal channels, wherein at least one signal channel is configured to process an electrophysiological signal that includes intracardiac ablation energy, along a signal path extending from an input port configured to receive the electrophysiological signal as an analog signal, via at least one adjustable gain element configured to amplify the electrophysiological signal with a gain according to a gain setting, and via an analog-to-digital (ADC) element configured to convert the analog signal into a digital signal corresponding to the electrophysiological signal, to an output port configured to provide the digital signal as an output;
a monitoring element configured to generate a monitoring signal representative of a magnitude of a DC component of the electrophysiological signal; and
a gain control element configured to generate a control signal in response to the monitoring signal, wherein the control signal is configured to control the gain setting of the adjustable gain element so as to cause a decrease in gain responsive to an increase in the magnitude of the DC component caused by activation of the intracardiac ablation energy and/or an increase in gain responsive to a decrease in the magnitude of the DC component caused by deactivation of the intracardiac ablation energy.

* * * * *

UNITED STATES PATENT AND TRADEMARK OFFICE
CERTIFICATE OF CORRECTION

PATENT NO. : 11,737,698 B2
APPLICATION NO. : 16/979792
DATED : August 29, 2023
INVENTOR(S) : Sigge Nejst Larsen et al.

Page 1 of 1

It is certified that error appears in the above-identified patent and that said Letters Patent is hereby corrected as shown below:

In the Claims

Column 13, Line 47 please delete "wherein the".

Signed and Sealed this
Third Day of October, 2023

Katherine Kelly Vidal
*Director of the United States Patent and Trademark Office*